United States Patent [19]
Baker et al.

[11] Patent Number: 4,887,458
[45] Date of Patent: Dec. 19, 1989

[54] HEMATOCRIT READER APPARATUS AND METHOD

[75] Inventors: Charles D. Baker, Sandy; Owen D. Brimhall, West Valley City; James E. Messinger, Salt Lake City, all of Utah

[73] Assignee: Separation Techology, Inc., Salt Lake City, Utah

[21] Appl. No.: 247,246

[22] Filed: Sep. 21, 1988

[51] Int. Cl.⁴ .................... G01N 33/48; G01N 1/00
[52] U.S. Cl. .................... 73/61.1 R; 73/61.4; 436/70
[58] Field of Search ............. 73/61.4, 64.1, 61.1 R, 73/149, 61 R; 210/782, 787; 128/637, 638; 422/58, 73, 59; 436/70, 63, 177; 364/413.07, 413.08, 413.09, 560; 33/143 B; 346/33 ME; 356/40

[56] References Cited

U.S. PATENT DOCUMENTS

| | | | |
|---|---|---|---|
| 2,973,580 | 3/1961 | Brown | 33/143 B |
| 3,218,719 | 11/1965 | Van Dyck et al. | 33/143 B |
| 3,416,361 | 12/1968 | Asnes et al. | 73/61 R |
| 4,122,607 | 10/1978 | Hopf | 364/560 |
| 4,156,570 | 5/1979 | Wardlaw | 73/747 |
| 4,163,615 | 8/1979 | Kwasman | 356/40 |
| 4,202,033 | 5/1980 | Strobel | 364/413.08 |
| 4,699,887 | 10/1987 | Abbott et al. | 73/61 R |

Primary Examiner—Hezron E. Williams
Attorney, Agent, or Firm—J. Winslow Young

[57] ABSTRACT

This invention is a semiautomatic hematocrit reader apparatus and method. A microhematocrit capillary tube is positioned under a movable cursor which is then moved along the length of the microhematocrit capillary tube. A switch is depressed to make a data entry at predetermined points along the length of a blood/-plasma sample in the microhematocrit capillary tube. The relative distances travelled across the packed cell volume versus the plasma is electronically calculated and displayed automatically.

5 Claims, 1 Drawing Sheet

HEMATOCRIT READER APPARATUS AND METHOD

BACKGROUND

1. Field of the Invention

This invention relates to apparatus for obtaining hematocrit readings and more particularly, to a semiautomatic hematocrit reader wherein an operator moves a cursor to identify the pertinent data points on a microhematocrit capillary tube and the device automatically calculates and displays the hematocrit reading.

2. The Prior Art

Blood consists of numerous components but can be roughly classified as including cells in a fluid matrix which is referred to generally as the plasma. The ratio of blood cells to plasma is known as the hematocrit of the blood and is an important parameter for diagnostic and consequent therapeutic purposes. Conventionally, hematocrit of a drop of blood is obtained by drawing the blood by capillary action into a microhematocrit capillary tube. The end of the capillary tube is plugged by being pushed into a putty-like compound such as a clay. The small plug of clay forms a sealing relationship in the end of the capillary tube. Separation of the blood cells from the plasma is achieved under very high centrifugal forces in a high speed centrifuge apparatus where several minutes of high speed centrifugation are required to achieve the desired degree of separation. Uniformity of results is obtained by consistency in the centrifugation processing of the blood sample in each capillary tube.

After centrifugation the capillary tube is compared with a chart that is a graphical representation of various hematocrit readings as a function of total volume of blood in the capillary tube. These charts are usually presented in a scroll-like configuration so as to accommodate the large amount of chart information in a relatively small space. Even a skilled operator must spend considerable time finding the correct total blood volume line and then moving the hematocrit tube to match the blood/plasma interface with the appropriate hematocrit reading line. Thereafter the operator determines the correct chart line and transcribe this reading to the appropriate medical chart or document.

From the foregoing it is readily apparent that valuable time is consumed and many opportunities for error occur not only in the matching of the capillary tube to the chart but also in the interpolation of the chart and in transcribing the information. Clearly, any significant error could prove catastrophic to a patient if the wrong therapeutic procedures were prescribed as a result of an erroneous hematocrit reading. In view of the foregoing, it would be an advancement in the art to provide a semiautomatic hematocrit reader apparatus whereby the operator simply moves a cursor to the various data entry points and the apparatus automatically calculates the hematocrit reading. Such a novel apparatus and method is disclosed and claimed herein.

BRIEF SUMMARY AND OBJECTS OF THE INVENTION

This invention relates to a semiautomatic hematocrit reader apparatus and method whereby the operator moves a cursor along the length of a capillary tube and makes data entries at the bottom, the blood cell/plasma interface and the top of the sample. The packed cell volume or hematocrit reading of the sample is automatically displayed on a display and can also be transmitted electronically into other data processing and storage equipment. The position of the cursor relative to the data entry points is measured automatically as the cursor is moved so as to provide ratio of the length of the packed cell volume and the plasma in the capillary tube.

It is, therefore, a primary object of this invention to provide improvements in apparatus for reading a hematocrit.

Another object is to provide improvements in the method of obtaining a hematocrit reading.

Another object of this invention is to provide a semiautomatic hematocrit reader wherein the hematocrit is automatically calculated as a function of relative distances a cursor is moved between data entry points.

These and other objects and features of the present invention will become more readily apparent from the following description in which preferred and other embodiments of the invention have been set forth in conjunction with the accompanying drawing and appended claims.

DETAILED DESCRIPTION

Figure 1:
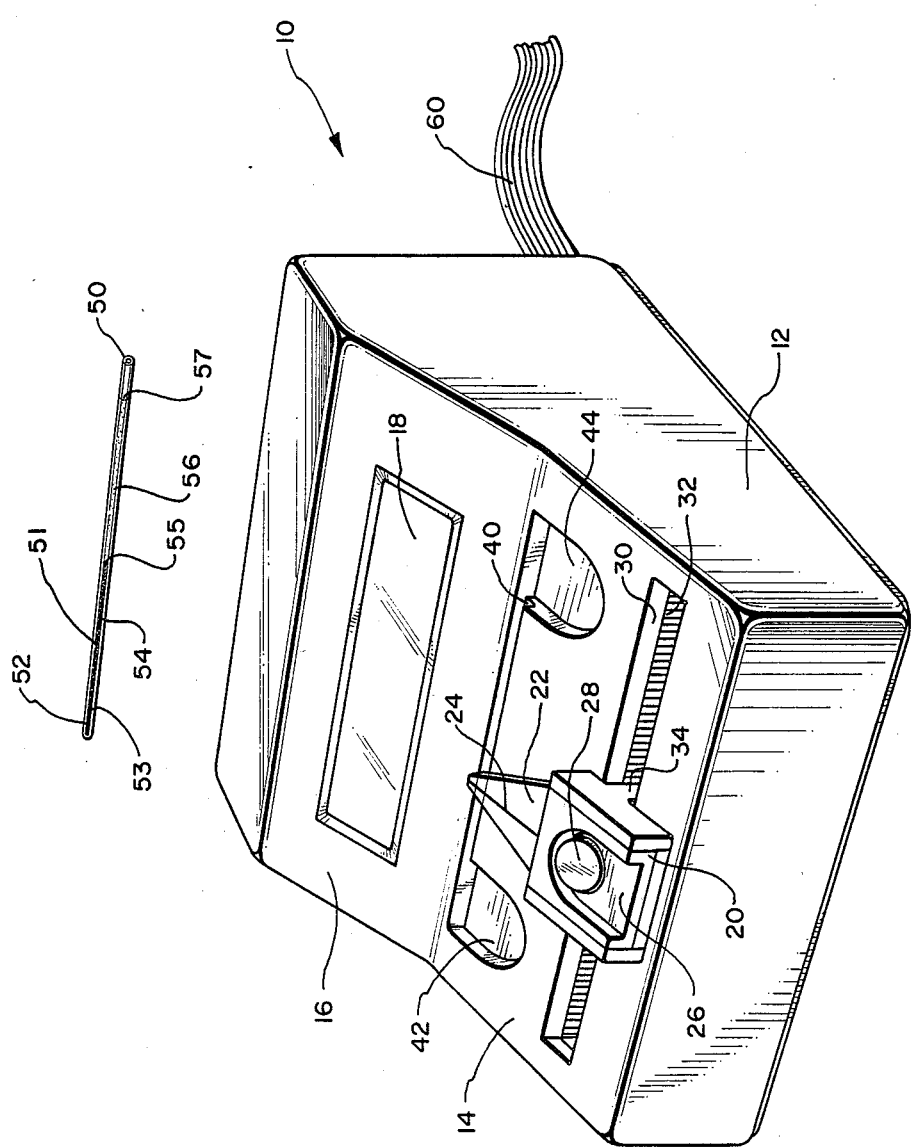
FIG. 1 is a perspective view of a presently preferred embodiment of the semiautomatic hematocrit reader of this invention shown in the environment of a microhematocrit capillary tube.

The invention is best understood by reference to the drawing wherein like parts are designated by like numerals throughout in conjunction with the following description.

The Apparatus

Referring now more particularly to FIG. 1, a presently preferred embodiment of the semiautomatic hematocrit reader of this invention is shown generally at 10 and includes a housing 12 having a working platform 14 and a face 16. A display window 18 is located on face 16 and can be any suitable display whether a diode array, or in the presently preferred embodiment, a commercially available liquid crystal display. A movable marker 20 is slidably mounted in a slot 30 in platform 14 and has mounted thereon a clear plastic extension 22 on which is scribed a cursor 24. Marker 20 includes a finger detent 26 with a data entry switch 28 in the end thereof.

A capillary tube-receiving channel 40 is formed at the juncture between platform 14 and face 16. Each end of channel 40 opens into finger recesses 42 and 44 the outer edges of which act as stops to the respective ends of channel 40. The base of channel 40 is raised slightly above the bottom of recesses 42 and 44 so as to provide a fulcrum against which a respective end of a capillary tube 50 may be pivoted so that the opposite end of capillary tube 50 is raised sufficiently to enable it to be grasped to remove capillary tube 50 from channel 40.

A reference 32 is mounted in slot 30 and provides an electronic feedback mechanism to indicate the relative position of marker 20 with reference 32. Reference 32 can be any suitable, conventional reference guide such as a resistive or a capacitive strip wherein the respective resistance or capacitance changes as a function of distance through which marker 20 is moved. However, in this presently preferred embodiment of hematocrit reader 10, reference 32 is fabricated from a strip of plastic material on to which is printed a plurality of uniformly spaced lines. A conventional optical counter (not shown) in marker 20 counts the number of lines passed as marker 20 is moved, the number of lines being calibrated in hematocrit reader 10 as a function of distance.

Hematocrit tube 50 is a conventional microhematocrit capillary tube into which a blood sample 51 has been drawn by capillary action. The bottom of hematocrit tube 50 is plugged with a clay plug 52 and the upper end of blood sample 51 forms a meniscus 57. Blood sample 51 has been subjected to the very high gravitational forces during centrifugation according to conventional techniques to produce a packed cell volume 54 at the lower end and a supernatant or plasma 56 at the other end with a blood/plasma interface 55 between the two fractions.

The Method

In practice the open end of hematocrit tube 50 is brought against a drop of blood where capillary action draws blood 51 into hematocrit tube 50. Hematocrit tube 50 is then punched into a layer of clay, putty, or the like, to form a seal with plug 52 in the bottom end. Hematocrit tube 50 is next placed in a conventional centrifuge apparatus (not shown) where blood sample 51 undergoes separation into the packed cell volume 54 and plasma 56 with blood/plasma interface 55 therebetween.

Hematocrit tube 50 is placed in channel 40 with plug 52 residing in the region of recess 44. Marker 20 is moved to the left until cursor 24 is collimated with plug/blood interface 53 at which time switch 28 is depressed to produce a first data entry point. Marker 20 is then moved to the right until cursor 24 is collimated with blood/plasma interface 55 and switch 28 is again depressed to produce the second data entry. Marker 20 is then moved again to the right until cursor 24 is collimated with meniscus 57 and switch 28 is depressed a third time for the final data entry point.

Calibration strip 32 provides an automatic input into hematocrit reader 10 as to the distances through which marker 20 is moved between data entry points. The electronics (not shown) in hematocrit reader 10 are conventional and are programmed so that after the third data entry has been made the hematocrit reading is automatically calculated and displayed in display window 18. This is done by simply comparing electronically the distance through which marker 20 (more particularly, cursor 24) is moved between bottom 53 and blood/plasma interface 55 then meniscus 57.

The data thus collected by this unique process can then be either transcribed into the appropriate records or transmitted electronically through wire bundle 60 to a suitable data storage/processor apparatus (not shown) as is conventional in the art. Power for hematocrit reader 10 can be either by internal battery, through wire bundle 60 from the storage/processor apparatus or from an independent power source (not shown).

Upon completion of the sample reading operation, the operator (not shown) presses either end of hematocrit tube 50 into recess to cause the fulcrum of the raised bottom of channel 40 to raise the opposite end of hematocrit tube 5 out of channel 40 where it can then be grasped and disposed of in a suitable manner.

In summary, hematocrit reader 10 provides a rapid, reliable and relatively error-free apparatus and method for reading a hematocrit and displaying and/or transmitting the reading for subsequent use. Advantageously, moderately trained technicians can be rapidly oriented in the proper and accurate operation of hematocrit reader 10.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A hematocrit reader for providing an indication of the ratio of packed cell volume relative to the plasma volume in a blood sample in a microhematocrit capillary tube wherein the blood sample has undergone centrifugation to produce a separation between the packed cell volume and the plasma comprising:

a channel for holding the microhematocrit capillary tube;

moveable marker means for movement along the length of the microhematocrit capillary tube, said moveable marker having a finger detent for moving said moveable marker;

cursor means mounted on said moveable marker for collimating the marker with selected positions on the microhematocrit capillary tube;

data entry means comprising a data entry switch in said finger detent for entering data at specific locations of the marker means as determined by said cursor means;

calibration means for coordinating the position of the marker means relative to the data entry points entered by the data entry means;

comparison means for comprising the distance the marker is moved between data entry points, the comparison means providing a hematocrit reading for the blood sample in the microhematocrit capillary tube.

2. The hematocrit reader defined in claim 1 wherein the cursor means is mounted to the moveable marker means.

3. A reader for a microhematocrit capillary tube comprising:

a housing, the housing containing electronic means for calculating a hematocrit reading of a microhematocrit capillary tube;

a slot in the housing for receiving the microhematocrit capillary tube;

a marker slidably mounted to the housing in conjunction with the slot, the marker having a finger detent for moving the marker and a cursor mounted to the marker adjacent the slot;

a calibration means adjacent the marker for determining the relative position of the marker;

a data entry switch in the finger detent on the marker for making a data entry into the electronic means in the housing when the cursor is collimated with preselected positions on a microhematocrit tube in the slot; and a display on the housing for displaying the hematocrit reading calculated by the electronic means in the housing.

4. A method for obtaining a hematocrit reading from a blood sample in a microhematocrit capillary tube wherein the blood sample has undergone centrifugation comprising:
  providing a receiving slot for a microhematocrit capillary tube;
  mounting a movable cursor adjacent the slot, the cursor having a finger detent, and moving a cursor along the length of the microhematocrit capillary tube;
  placing a data entry switch in the finger detent on the movable cursor and making data entry points at three predetermined positions along the length of the microhematocrit tube by depressing the data entry switch in conjunction with moving the cursor between the predetermined positions;
  calibrating the position of the cursor as a function of the data entry points; and
  calculating the relative distances travelled by the cursor along the length of the microhematocrit tube as a function of the ratio of the distance between a first and a second data entry points and the distance between the second and a third data entry point.

5. The method defined in claim 4 wherein the mounting step includes slidably mounting the cursor to a housing along with a computing means for said calculating step.

* * * * *